United States Patent [19]

Weinblatt

[11] Patent Number: 4,582,403

[45] Date of Patent: Apr. 15, 1986

[54] HEAD MOVEMENT CORRECTION TECHNIQUE FOR EYE-MOVEMENT MONITORING SYSTEM

[76] Inventor: Lee S. Weinblatt, 797 Winthrop Rd., Teaneck, N.J. 07666

[21] Appl. No.: 586,215

[22] Filed: Mar. 5, 1984

[51] Int. Cl.⁴ .............................................. A61B 3/14
[52] U.S. Cl. ................................................ 351/210
[58] Field of Search ....................... 351/205, 209, 210

[56] References Cited

U.S. PATENT DOCUMENTS 3,542,457 11/1970 Balding et al. ................ 351/210 X

*Primary Examiner*—Rodney B. Bovernick
*Attorney, Agent, or Firm*—Thomas Langer

[57] ABSTRACT

A technique is disclosed to provide eye movement measurement in which the eye position signal is corrected for head movement. A reference point and reference point monitor means are provided one of which is fixed relative to the viewer's head and the other is fixed relative to the screen. An error signal is generated when movement of the reference point is sensed by the reference point monitor means. The error signal is combined with the eye movement measurement signal to obtain a corrected reading. This technique is usable with eye movement monitoring equipment which is of the head-mounted type and that which is of the stationary type.

6 Claims, 3 Drawing Figures

HEAD MOVEMENT CORRECTION TECHNIQUE FOR EYE-MOVEMENT MONITORING SYSTEM

BACKGROUND OF THE INVENTION

This invention is directed to a technique for monitoring the eye movements of a subject viewing a certain scene in order to determine at what portion of the scene the subject is looking and, more particularly, the invention enables the signals obtained by the eye-movement monitoring equipment to be corrected for movement of the subject's head.

Eye-movement monitoring equipment is in use for a variety of purposes. In the medical field, it is a valuable tool for the diagnosis of visual and mental impairment. In the field of advertising, subjects can be tested for their reactions (e.g. interest, readership, reexamination, recall) to various forms of advertisements such as magazine ads, billboards, television ads and point-of-purchase displays. Other actual and potential uses exist in sports, the military, and school reading classes.

The measurement of eye movement can be done based on any one of a number of principles. These are dicussed in the article "Methods and Designs, Survey of Eye Movement Recording Methods" by Lawrence R. Young and David Sheena in Behavior Research Methods & Instrumentation 1975 Vol. 7(5) pgs 397–429. The principle utilized in the present invention is "corneal reflection". Briefly, incident light is reflected by the convex surface of the corneal bulge in a pattern of diverging light. This is imaged through a concave lens into a sensor such as a video camera, and the resulting signal is used to obtain a position measurement.

Eye-movement monitoring apparatus using the corneal reflection principle can be divided into the following two categories: a stationary type and a head-mounted type. In the former, a stationary light source directs a light beam at the eye. The beam reflected by the cornea is detected by a sensor, also stationary. See pages 402–403 of the above-mentioned article by Young and Sheena, the article "Eye Fixations Recorded on Changing Visual Scenes by the Television Eye Marker" by J. F. Mackworth and N. W. Mackworth in the Journal of the Optical Society of America Vol. 48, No. 7, July, 1958, pgs 439–445, and U.S. Pat. No. 4,075,657. In the second category of eye-movement monitoring equipment, both the light source and sensor are mounted on the subject's head. Such equipment has various advantages over the stationary variety in terms of, for example, size, weight, versatility, cost, and portability. Nevertheless, it works basically the same way in that a beam of light from a source is reflected off the cornea and into a sensor. Examples are found in pages 404–409 of the Young and Sheena article as well as U.S. Pat. Nos. 4,102,564 and 3,542,457.

The signals from the eye-movement monitoring sensor must, of course, be calibrated and suitably processed to correlate the subject's eye movements with a particular portion of the scene viewed. This is done by well known circuitry. In systems in which the eye movements and scene are shown simultaneously on a video monitor, the positioning circuitry responsive to the eye movement signals superimposes a cursor over the scene.

One disadvantage of eye-movement monitoring techniques is the requirement to eliminate, or certainly sharply minimize, the head movements of the subject. Such head movement produces an erroneous interpretation of what portion of the scene is being viewed by the subject. The impact of head movement on the accuracy of measuring eye movement with stationary type equipment is well known. A mathematical analysis can be found on pages 402–403 of the Young and Sheena article. U.S. Pat. No. 3,712,716 mentions that a lateral head movement of 0.2 mm while viewing an object two meters away changes the position being looked at, so far as the measuring apparatus is concerned, by 35 mm. A similar analysis can, of course, be readily made for the head-mounted type of eye movement monitoring equipment.

In order to prevent such erroneous readings, various devices have been used to restrict head movement. This includes chin holders, bit boards and head straps. In addition, some movement detection and correction techniques are also known as disclosed on pages 420–423 of the Young and Sheena article. However, the head-movement restriction devices are uncomfortable, particularly if the subject is confined for any significant period of time. Such discomfort can cause distraction and this also detracts from the results obtained with the eye-movement monitoring equipment.

The known signal correction techniques are also unsatisfactory because the required devices and circuitry are too complex and costly. In addition, the overall arrangement can be bulky and, therefore, not well suited to work in settings requiring portability.

SUMMARY OF THE INVENTION

The general object of the invention is to provide more accurate eye-movement monitoring equipment.

A more specific object of the invention is to provide eye-movement monitoring equipment which corrects for head movement of the subject.

Another object of the invention is to provide a correction technique for head movement of the subject which can be used with both stationary and head-mounted eye-movement monitoring.

Still another object of the invention is to provide a correction technique with the above subjects which is compact, relatively inexpensive, and easy to operate.

These and other objects of the invention are attained with eye movement monitoring apparatus for determining the point on a displayed scene at which a viewer is looking comprising: a light source for aiming a light beam at the viewer's eye; a sensor for detecting said aimed light beam reflected off the eye and generating a sensed position signal; circuitry for converting the sensed position signal to a processed eye movement position signal; means for measuring the head movement of said viewer to generate a head position signal; and means for combining the head position signal and the processed position signal to provide a corrected eye movement position signal; said head movement measurement means comprising a reference point and a reference point monitor means, one of said reference point and reference point monitor means being on the viewer's head and the other being in fixed relationship to the scene being viewed, said reference point monitor means providing a signal when it senses movement between itself and the reference point.

According to another aspect of the invention an apparatus is provided for use with eye movement measuring means to correct for head movement of the subject viewing a scene as his eye movements are being measured, said apparatus comprising: a reference point and a reference point monitor means; one of said reference point and the reference point monitor means being affixed to the viewer's head and the other being placed in fixed relationship to the scene being viewed; means for storing an initial head position signal; and means coupled to the reference point monitor means and the storing means for generating a head movement compensation signal.

BRIEF DESCRIPTION OF THE DRAWINGS

The invention is related to eye-movement monitoring equipment and provides a techniques which compensates for head movement of the subject, as described in detail in connection with the following drawings, of which.

DETAILED DESCRIPTION OF THE DRAWINGS

To correct for head movement of the subject while his eye movements are being monitored, a means is provided in accordance with this invention to obtain a signal indicative of such head movement. One head movement indicating means is provided for the stationary type of eye-movement monitoring equipment, and another for the head-mounted type. These are now discussed in detail with reference to FIGS. 3 and 4.

Figure 3:
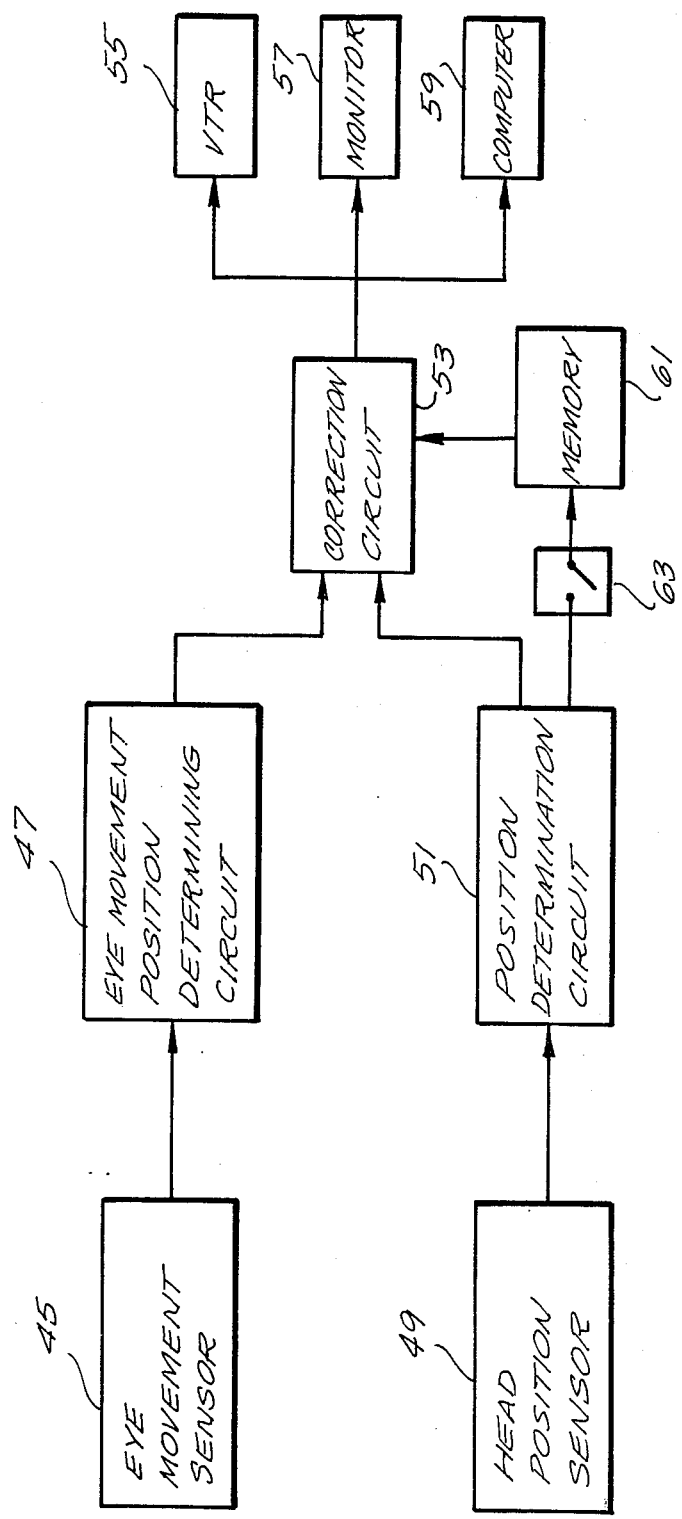
FIG. 3 is a block diagram of the circuitry for providing a head-movement correction to known eye-movement monitoring equipment.

An arrangement in accordance with the invention usable with the stationary type of eye-movement monitoring equipment is depicted in FIG. 3. As is conventional, a light source 21 is provided to cooperate with sensor 23. Light source 21 is directed at eye 25 of the subject, and the reflected beam is detected by sensor 25. In the preferred embodiment, light source 21 emits infrared light while sensor 25 is a suitable video camera. In addition to these conventional elements of eye-movement monitoring equipment, the arrangement of the invention includes another light source and another sensor. Light source 27 is aimed at a selected spot (discussed below) of the subject's head, and light reflected off that spot is detected by sensor 29. In the preferred embodiment, source 27 emits fluorescent or single spectrum light and sensor 29 is a suitably matched video camera. These are readily available and no further details are, therefore, deemed necessary.

In accordance with the invention, the subject's head is provided with some means to reflect light from light source 27 to sensor 29. In the preferred embodiment this means is reflective and preferably an invisible ink dot, 31, applied to the forehead of the subject. As the subject moves his head, light reflected off the ink dot will vary thus providing a signal indicative of head movement. The details of how this signal is used are provided in connection with the discussion below of FIG. 5.

FIG. 4 depicts an arrangement for head-mounted eye-movement monitoring equipment. As described in U.S. patent application Ser. No. 486,031 filed Apr. 18, 1983, which is hereby incorporated by reference, several elements of the equipment are mounted on an eyeglass frame, 33, worn by the subject. Light source 35 and sensor 37 cooperate to, respectively, aim a light beam at the subject's eye and detect the reflected light, as discussed in detail in the just mentioned U.S. patent application. Also mounted on frame 31 is a scene sensor 39. In use, as the frame 3 is worn by the subject, sensor 39 is aimed at screen 40 being viewed by the subject. Signals from sensors 37 and 39 are conveyed, as by fiber optics, to circuitry disclosed in the above-mentioned U.S. patent application. It should be understood that sensor 39 is not essential to this invention, and certainly not in the described way of being mounted on the frame 31. Other techniques exist for providing the same signal. See, for example, the above-mentioned Young and Sheena article, pages 404–405.

In addition to the known arrangement jsut described, and in accordance with the invention, another scene sensor, 41, is affixed to frame 31. This sensor can be a lens, or a CCD device. Both are, of course, well known and no specific details are deemed necessary. Suffice it to say that sensor 41 must be small and light, just like sensor 39. Sensed signals from sensor 41 are also, in the preferred embodiment, conveyed to appropriate circuitry (described below) by fiber optics.

The arrangement of the invention also includes a point of reference on the screen at which sensor 41 is aimed. Such a point of reference is a dot on screen 40 placed at any selected spot. In the preferred embodiment, registration dot 43 must have a unique characteristic to distinguish it from other dots on the screen as the scene is being displayed to the subject. For example, dot 43 might emit or reflect infrared or ultraviolet light. Sensor 41 is, of course, adapted to be sensitive only to that characteristic of dot 43. In the preferred embodiment, dot 43 is infrared.

Turning now to the circuitry depicted in FIG. 5, eye movement sensor 45 is coupled to the input of eye-movement position determining circuit 47. Sensor 45 is sensor 23 of FIG. 3 for one embodiment and sensor 39 of FIG. 4 for the other embodiment. Sensor 45 includes not only the actual sensing device, but the video camera to which the detected signal is input. It is the output of such video camera that is, in turn, connected to position circuit 47. Position circuit 47 can be any one of a number of well known circuits.

Figure 1:
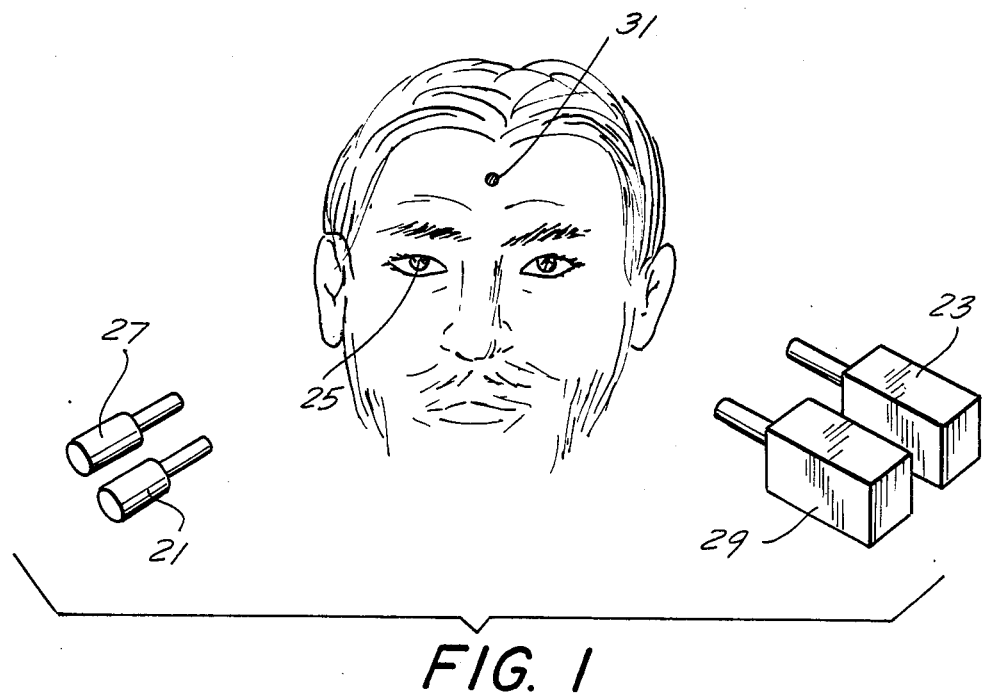
FIG. 1 shows a stationary type of eye-movement monitoring equipment modified to enable the sensing of head movement.
Figure 2:
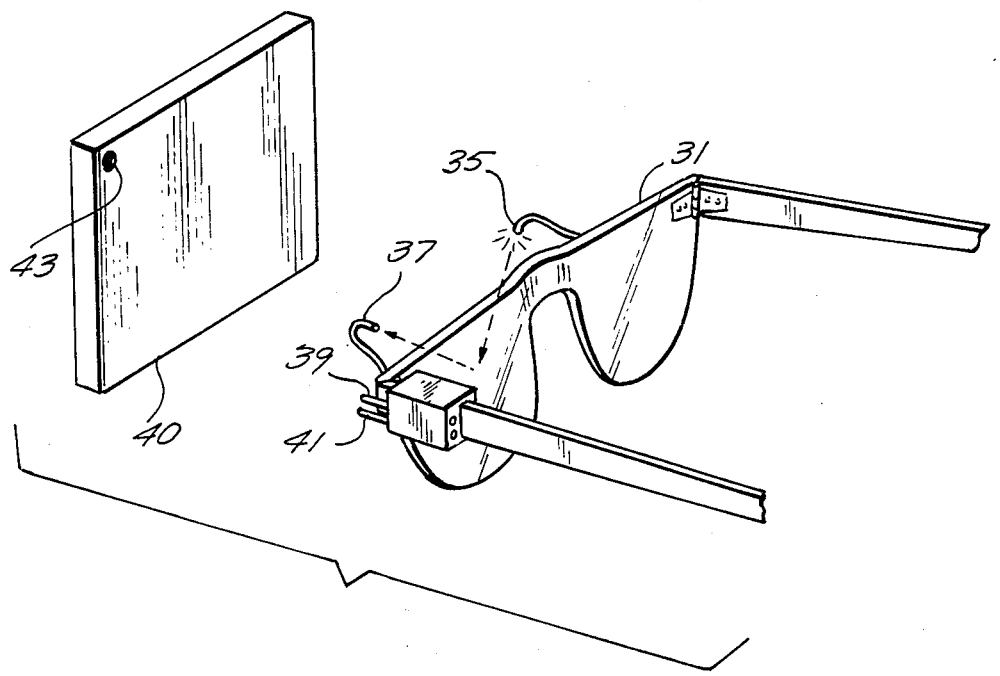
FIG. 2 shows a head-mounted type of eye-movement monitoring equipment modified to enable the sensing of head movement.

Included in the arrangement of the invention is head position sensor 49. Sensor 49 comprises sensor 29 of FIG. 2 for one embodiment and sensor 41 for the other embodiment. It should be understood that sensor 49 includes not only the actual sensing devices, but also the video camera to which the detected signal is input. It is the output signal of the video camera which is, in turn, input to position circuitry 51.

Eye-movement position determination circuit 47 and head position determination circuit 41 each have their output connected to the input of correction circuit 53. Correction circuit 53 combines the signals and provides an output signal corrected for head movement of the subject. The output of correction circuit 53 is connected to video tape recorder (VTR) 55, a video monitor 57, and a computer 59. VTR 55 records the signals from correction circuit 53 for use in subsequent analysis. Monitor 57 is useful to view the eye movement representation, such as a cursor, which is superimposed in a well known manner on the screen being viewed by the subject, while computer 59 can be used to do an automatic analysis. It can, for example, automatically provide desired data about the detected eye movements such as percentage of time of eye fixation, percentage of time eye fixed on particular points of screen, pattern of eye movement, etc. It should be clear that the latter forms no part of the invention and is diclosed as a possible use of the signals obtainable with eye-movement monitoring equipment.

In addition to the above-discussed elements shown in FIG. 5, memory circuit 61 is provided. It has its input coupled via switch 63 to the output of head position determining circuit 51 and its output connected to correction circuit 53. Memory 61 has sufficient capacity to store the position of ink dot 31 in FIG. 3 or registration dot 43 in FIG. 4. The position is entered into memory 61 during calibration of the equipment, which will now be described in detail.

For the stationary type of eye-movement monitoring equipment, the subject's head is fixed in place with a removable chin support, bite board, or head strap. The light source 27 is aimed at ink dot 31, and sensor 29 is positioned to detect the light reflected off the dot. For the head mounted type of eye-movement monitoring equipment, a signal from the head position sensor (29 or 41) is available.

Continuing now with the calibration for both types of eye-movement monitoring equipment, the signal from the head position sensor (29 or 41) is input to head position determination circuit 51 and a head position signal is input to memory 61. Switch 63 is momentarily closed for this purpose. Once the head position signal is stored, it is opened and remains so during operation of the equipment for this particular subject.

The eye movement detection devices are then positioned and the circuitry calibrated as described in the prior art cited in the Background portion. Briefly, the light source, 21 in FIG. 3 or 35 in FIG. 4, is aimed at the eye and the sensor, 23 in FIG 3 or 37 in FIG. 4 is aimed so as to detect the light reflected off the eye. Appropriate optics (not shown) are then adjusted to correct for peculiarities of the eye such as curvature end protrusion, as well as to set the field of view so it corresponds to that provided by the scene sensor. The scene sensor is also adjusted as needed, particularly on the head-mounted eye-movement monitoring equipment.

Once the calibration is complete, the head fixation means (e.g. bite bar) is removed for the comfort of the subject, switch 63 is opened, and operation begins.

In operation, the head position signal from circuit 51 and the stored head position signal from memory 61 should be the same if the subject has not moved his head. When these signals are equal, they cancel each other and the output from eye-movement position determing circuit 47 is what is output by correction circuit 53. If, however, the subject moves the head, the signals from circuit 51 and memory 61 are no longer equal and correction circuit 53 detects a component signal indicative of the direction and extent of head movement. This component signal is combined with the signal from circuit 47 to generate a corrected eye movement position signal.

It should be understood that the above is not meant to limit the invention to only what is described. Several modifications would be readily apparent. For example, the manner in which the stored head position signal is combined with the actual head position signal can be varied to include circuitry totally within circuit 51, or to a head position correction circuit separate from circuit 53 to which only the stored and actual head position circuits would be input. The output would then be combined with the eye position signal. Clearly, this can be done digitally or with analog circuitry. All of these mentioned modifications and others are intended to be part of the invention as defined by the following claims.

I claim:

1. Eye movement monitoring apparatus for determing the point on a displayed scene at which a viewer is looking comprising:
    a light source for aiming a light beam at the viewer's eye;
    a sensor for detecting said aimed light beam reflected off the eye and generating a sensed position signal;
    circuitry for converting the sensed position signal to a processed eye movement position signal;
    means for measuring the head movement of said viewer to generate a head position signal; and
    means for combining the head position signal and the processed position signal to provide a corrected eye movement position signal;
    said head movement measurement means comprising a reference point and a reference point monitor means, one of said reference point and reference point monitor being on the viewer's head and the other being in fixed relationship to the scene being viewed, said reference point monitor means providing a signal when it senses movement between itself and the reference point.

2. The apparatus of claim 1 wherein the head movement monitoring means comprises calibration means coupled to the reference point monitor means for storing an initial head position signal and a switch between the reference point monitor means and the calibration means, said switch being closed only during calibration.

3. The apparatus of claim 1, wherein the light source and sensor are stationary, said referenc point comprising a dot of reflective substance applied to the viewer's forehead, said reference point monitor means comprising another light source for directing a beam aimed at said dot and another sensor for detecting the light beam reflected off said dot.

4. The apparatus of claim 1, wherein the light source and sensor are mounted on the viewer's head, said reference point monitor means comprising another light sensor mounted on the viewer's head, said reference point comprising a dot within the field of view of said another light sensor.

5. The apparatus of claim 4 wherein the light source, light sensor and the other light sensor are all mounted on an eye glass frame.

6. Apparatus for use with eye movement measuring means to correct for head movement of the subject viewing a scene as his eye movements are being measured, said apparatus comprising:
    a reference point and a reference point monitor means;
    one of said reference point and the reference point monitor means being affixed to the viewer's head and the other being placed in fixed relationship to the scene being viewed;
    means for storing an initial head position signal; and
    means coupled to the reference point monitor means and the storing means for generating a head movement compensation signal.

* * * * *